United States Patent [19]

Rubin

[11] 4,198,862
[45] Apr. 22, 1980

[54] APPARATUS FOR CIRCULATING A PORTION OF THE LIQUID CONTENTS OF A TANK FOR ANALYSIS AND OBTAINING REPRESENTATIVE SAMPLES

[75] Inventor: Isadore E. Rubin, South Orange, N.J.

[73] Assignee: Pilot Unit Products, Inc., South Orange, N.J.

[21] Appl. No.: 6,639

[22] Filed: Jan. 26, 1979

[51] Int. Cl.² ............................................. G01N 1/14
[52] U.S. Cl. ................................................... 73/421 B
[58] Field of Search ............... 73/421 R, 421 B, 422 R

[56] References Cited

U.S. PATENT DOCUMENTS

| | | | |
|---|---|---|---|
| 2,934,959 | 5/1960 | Johnson | 73/421 B |
| 3,188,565 | 6/1965 | Kolb. | |

FOREIGN PATENT DOCUMENTS 1105227  10/1958  Fed. Rep. of Germany ......... 73/421 B Primary Examiner—S. Clement Swisher
Attorney, Agent, or Firm—Lerner, David, Littenberg & Samuel

[57] ABSTRACT

A sampling pump having a helix rotor is immersed below the surface of the liquid composition being prepared within a large tank in which the contents are mixed, agitated and heated or cooled by various means. A drive motor positioned above the tank imparts rotation to the helix pump rotor through an elongated coupling shaft. A stream of the liquid is lifted vertically upward through an elongated extension housing inside the vessel and then through a conduit external to the vessel and ultimately returns the liquid stream to the tank. Analytical instrumentation may be provided at intervals along the external conduit for performing desired chemical and physical analyses. A three-way valve in the conduit is provided to selectively dispense samples for analysis elsewhere, without interrupting the stream flow and thus insuring the representative character of the sample. A stuffing box assembly is employed for completely isolating the drive and/or the motor from the liquid contents. The sample pump and external conduit are positioned so that when the tank is emptied the sample pump and the external conduit are drained of liquid.

16 Claims, 5 Drawing Figures

APPARATUS FOR CIRCULATING A PORTION OF THE LIQUID CONTENTS OF A TANK FOR ANALYSIS AND OBTAINING REPRESENTATIVE SAMPLES

BACKGROUND OF THE INVENTION

Many liquid compositions, plastic material, and the like, are prepared in large batches and typically require controlled addition of ingredients, a number of hours of agitation, heating, pressurization, and the like. Since it is most economical to prepare such compositions in relatively large quantities, it is also important to be assured that the batch being prepared meets all of the desired criteria, such as purity, density, viscosity, consistency, pH, color, etc., and that the batch contains all of the correct individual ingredients in their proper proportions.

It is thus quite important to constantly monitor the batch as it undergoes preparation to be assured that the batch meets all of the desired criteria during each phase of preparation, and further to enable appropriate corrective measures to be undertaken promptly to prevent the rather expensive loss of a batch as a result of failure to undertake proper monitoring and corrective measures, when necessary. Many batches under preparation require that certain elevated temperature levels and/or pressure levels be maintained throughout the mixing and preparing phases, placing severe restraints on the type of apparatus which may be utilized to extract a sample.

The tank containing the batch being monitored is typically rather tall, i.e., taller than the average person. The ingredients are generally added at the top of the tank. The exhaust ducting (if any) and often the heating fluids and/or coolants are normally inserted and/or removed from the top of the tank. As a result it is most advantageous to locate all instrumentation and analytical instrumentation in the same area, at the top of the tank, and to deliver the sample(s) at this area or level.

Such laboratory facilities are frequently located at the level of the top of the tank and extracting samples from the bottom is time consuming. The laboratory is frequently combined with a control panel. In order to extract a sample from the bottom of the tank the operator must absent himself from observation of the control panel for a considerable time if he goes downstairs to extract a sample from the lower portion of the tank.

Also samples drawn from a stagnant section, such as tank protuberance, nozzle or pipe extending from the vessel or other such arrangement requires withdrawal of sufficient liquid to clear the space of stagnant liquid. Then a separate more representative sample of the batch may be obtained. The sampling system to be described herein-below provides for a continuous rapid flow and thus a continuously representative sample without the necessity of withdrawing (and generally discarding) unrepresentative material.

BRIEF DESCRIPTION OF THE INVENTION

The present invention is characterized by providing a method and apparatus for preferably continously lifting a liquid stream from a veseel or tank, delivering the sample flow to an analysis conduit for analytical evaluation and/or for the selective extraction of a small sample quantity, when desired, and return of the liquid stream to the main batch processing tank. The liquid in the tank is lifted by a helix-type pump which, although operating at a low speed, provides a flow rate which is quite adequate for on-line analytical testing and for sampling purposes.

When the batch is completed and the vessel or tank is emptied the sample pump, because of its construction drains of liquid.

In addition, the novel pump design allows for the simple and rapid removal and disassembly of the helix pump for cleaning between batch changes, if necessary.

The pump and its manner of operation provides for the lifting of the liquid sample at a more than adequate flow rate while totally isolating the pump drive motor from the liquid contents by means of a stuffing box assembly.

An external conduit is adapted to deliver the sample to a region where it undergoes on-line analysis and return of the sample directly to the processing tank, yielding a simple and yet effective system for obtaining the desired analytical observations at a location removed from the interior of the batch processing tank and in a manner in which the sample extracting apparatus provides no interference whatsoever with the normal batch processing operations. By means of a three-way valve in the external conduit, a sample may be withdrawn from the continuously circulating, and thus representative stream and removed to a laboratory for analysis.

BRIEF DESCRIPTION OF THE FIGURES AND OBJECTS OF THE INVENTION

It is therefore one object of the present invention to provide a novel method and apparatus for extracting liquid samples from a large tank to facilitate non-contaminating for non-modifying analysis and thereafter to directly return the sample to the tank, or alternatively to provide means for removing a sample completely from a continuously moving stream to permit laboratory analysis.

Another object of the present invention is to provide apparatus of the type described hereinabove wherein means are provided for lifting the sample from the tank by a motor driven pump means and for isolating the motor from the tank to prevent contamination of the liquid contents or damage to the motor, and to permit use of the sampling apparatus with closed pressurized or evacuated tanks.

Still another object of the present invention is to provide novel apparatus of the type described hereinabove in which a helix pump is utilized for lifting the liquid sample to the location at which analyses takes place.

The above as well as other objects of the present invention will become apparent while reading the accompanying descriptions and drawings, in which.

DETAILED DESCRIPTION OF THE FIGURES

FIGS. 1 through 4 show a system 10 embodying the principles of the present invention, comprised of a large batch processing tank (i.e., pressure vessel) 11 suitable for preparing large batches of a chemical composition. For example, the tank may have a liquid capacity in the range of from 50 to 20,000 gallons and be adapted for mixing a variety of ingredients, for example, a resin, a pharmeceutical preparation etc. It is typical to prepare such batches commercially in quantities of from 100 to 15,000 gallons per batch. Although this technique has inherent economies, it is nevertheless important to continuously monitor the batch during preparation in order to be assured that all chemical and physical characteristics which are critical to the desired quality of the end product are maintained in order to avoid the possibility of having to discard the entire batch for failure to meet the desired quality standards.

Figure 1:
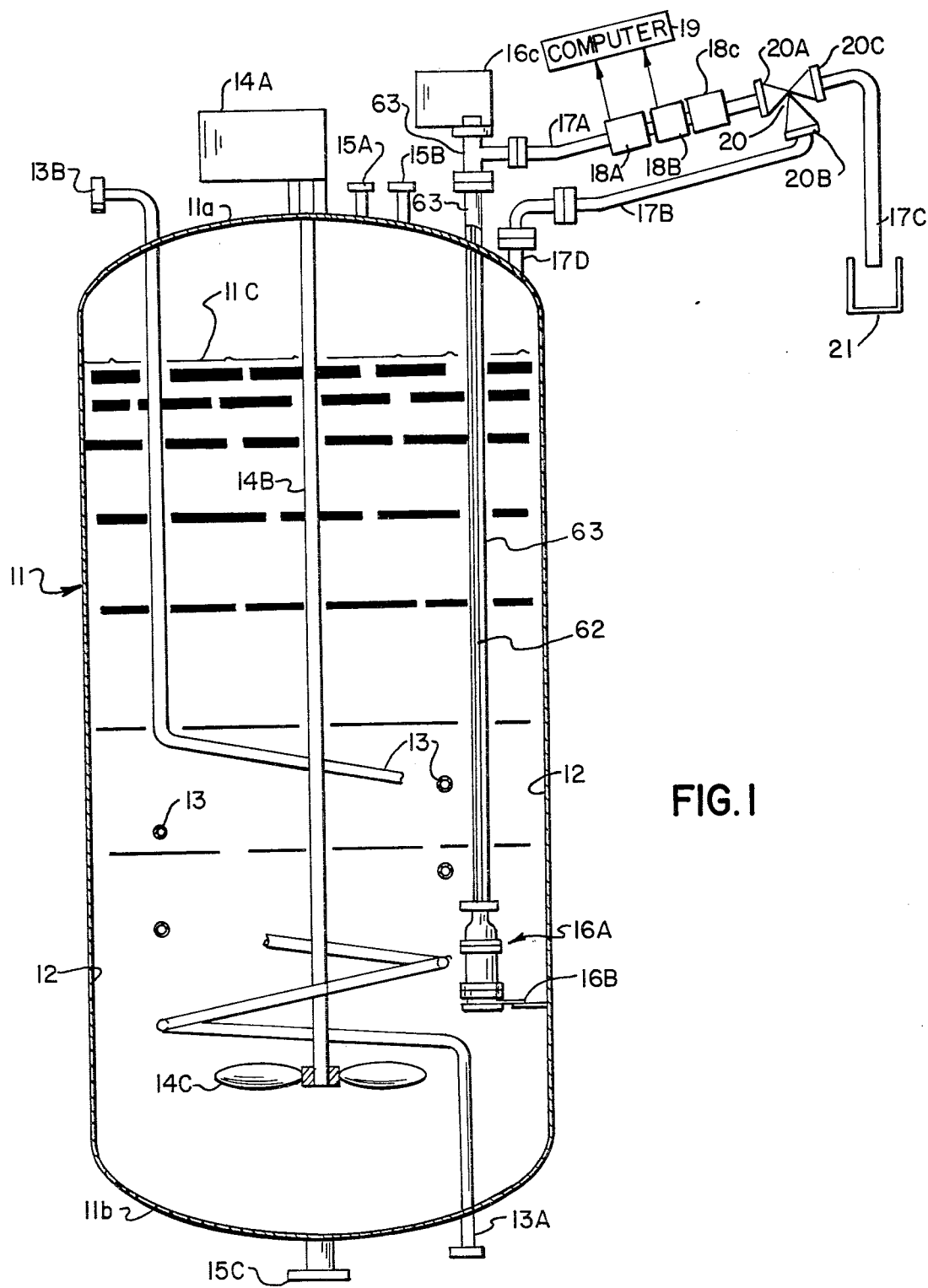
FIG. 1 shows a simplified block diagram of a system embodying the principles of the present invention.

In batch processes of the type described, a closed container 11, frequently of the pressure vessel type, is required to contain the materials, especially in the gaseous state. Operations at elevated temperatures, above atmospheric pressures or vacuum may be required. Noxious fumes may be generated. The most typical vessels employed are vertical cylindrical vessels 11 (Note: items shown on sketch not in text so I added it here) with dished tops 11a and bottoms 11b, as illustrated in FIG. 1. Other shaped vessels or vessels in different positions (e.g., horizontal cylindrical) may also be used with this system.

Heating and/or cooling operations are frequently required. These capabilities may be obtained by a great variety of means, some of which are as follows: direct fired furnace, hot oil jacket; electrical resistance heater; steam or Powtherm vapors in a jacket or coil; liquid heat exchange fluids such as oils, molten salt, etc.; and electric induction heat. Cooling or heating may be obtained by use of coils or other conduits 13 inserted into the vessel, as illustrated in FIG. 1. For a liquid heat transfer medium the inlet port would be 13A and the outlet port 13B. Mixing is also generally required and is obtained as illustrated by agitator drive 14A, agitator shaft 14B and agitator impeller 14C of FIG. 1. Insertion of ingredients may be accomplished by means of inlet connections such as 15A. Vapors may be carried out by connections such as 15B and liquid in the vessel may be drained through an outlet drain 15C. Any of these appurtenances may be provided and operated in conjunction with the sample system 10.

It is important to constantly monitor the batch being processed. Quite often the information needed requires that the analyses be performed away from the processing area and within a laboratory type environment. All of these objectives are accomplished by the apparatus of the present invention which comprises a helix pump assembly 16A mounted within processing tank 11 and lowered to a depth sufficient to assure that the operating elements of the pump lie beneath the surface of the liquid batch being processed. Typical liquid level is indicated at 11C. The pump assembly 16A is retained in position against vibrational and other forces such as those imposed by the action of the mixer by means of a bracket 16B.

The pump is connected with a motor and drive shown schematically as 16C through shaft 16D. The motor and drive are located a spaced distance above the pump 16A. For example, in a multistory processing plant, the batch processing tank 11 may be located upon the ground floor and the pump drive 16C may be located at the second or even the third floor of the facility. Hollow extension housing 63 extends between the lower end of the drive 16C and the upper end of pump 16A. The connections of both ends of 63 are air- and water-tight. At the lower connection between housing 63 and pump assembly 16A there is a flanged connection. At the upper connection of housing 63 to the pump drive 16C there is a seal, as will be discussed hereinafter. Although shaft 62 extends through the extension housing 16E, there is sufficient clearance to enable the free, upward flow of liquid therethrough. Although pipe sections 63 and 17D are shown as being rather short, they may be of any desired length.

Extension housing 63 is joined to an outlet pipe 17A through T-connection 69. A series of analytical instrumentation devices 18A, 18B, etc., may be arranged in cascade fashion along the outlet pipe 17A so as to be directly accessible to the fluid flowing upwardly through housing 63 in order to constantly monitor the critical conditions of the batch such as temperature, viscosity, density, acidity and pressure, to name just a few. One or more of the instruments may be coupled with a computer 19 which may, for example, be a batch processing computer adapted to exert control over the batch in process. This computer could automatically control each step of the process and automatically adjust or modify any process step, when necessary, dependent upon the readings constantly being taken during the processing operation, and thereby assure that remedial action is taken promptly and reliably.

Conduit 17A is connected to a three-way valve 20 at connection 20A. The other two connections of the three-way valve means 20B and 20C are attached respectively to conduits 17B and 17C. For those analyses requiring the extraction of a sample, valve 20 may be moved to a first position coupling pipe 17A to conduit 17C to extract a liquid sample for use in analytical equipment which, either due to the nature of the material or due to the nature of the analysis to be performed, requires that the analysis be performed in an off-line fashion. The three-way valve means 20 may be either mechanically, electrically or pneumatically operable and is preferably capable of two types of operation. The valve is of such a nature (i.e. a three-way valve) such that flow is always permitted in some direction. In the case illustrated in FIG. 1, flow is either back to the vessel 11 via conduit 17B or to a sample receiver 21 via conduit 17C or a combination of both. Since some analyses are required at rather regular intervals, such analyses may be instituted by means of a program in computer 19 which is preferably adapted to control the time at which the sample is taken and the interval of time at which the valve means 20 is operated to determine the size of the sample extracted. Manual control or manual overide of the valve means 20, on the other hand, allows the extraction of samples which may be required on other than a periodic or emergency basis.

The return conduit 17B is coupled to the batch processing tank 11 through a suitable coupling 17D opening into vessel 11, thereby providing a closed-loop path for the return flow of the fluid sample by operating valve means 20 to a second position to enable the fluid stream to flow from pipe 17A to pipe 17B. The drive 16C and pump 16A are operated continuously to ensure smooth flow of the liquid sample through the closed-loop path of pipes 17A and 17B since turbulent flow may affect the accuracy of the conditions being monitored, as well as assuring that the closedloop branch comprised of 69, 17A, 20, 17B and 17D remains free and unclogged by virtue of the constant fluid flow. If the pump 16A is stopped, the system is so arranged that all material in the pump, the analytical devices or the conduits 17A and 17B will drain back down to the liquid level in the tank. The conduits 17A and 17B are thus arranged in a sloping fashion as shown. When the vessel 11 is emptied, the material in the extension housing 63 and the helix pump assembly 16A will drain into the vessel. In addition, the helix pump 16A and its parts may be flushed with any solvent compatible with the system.

Figure 2:
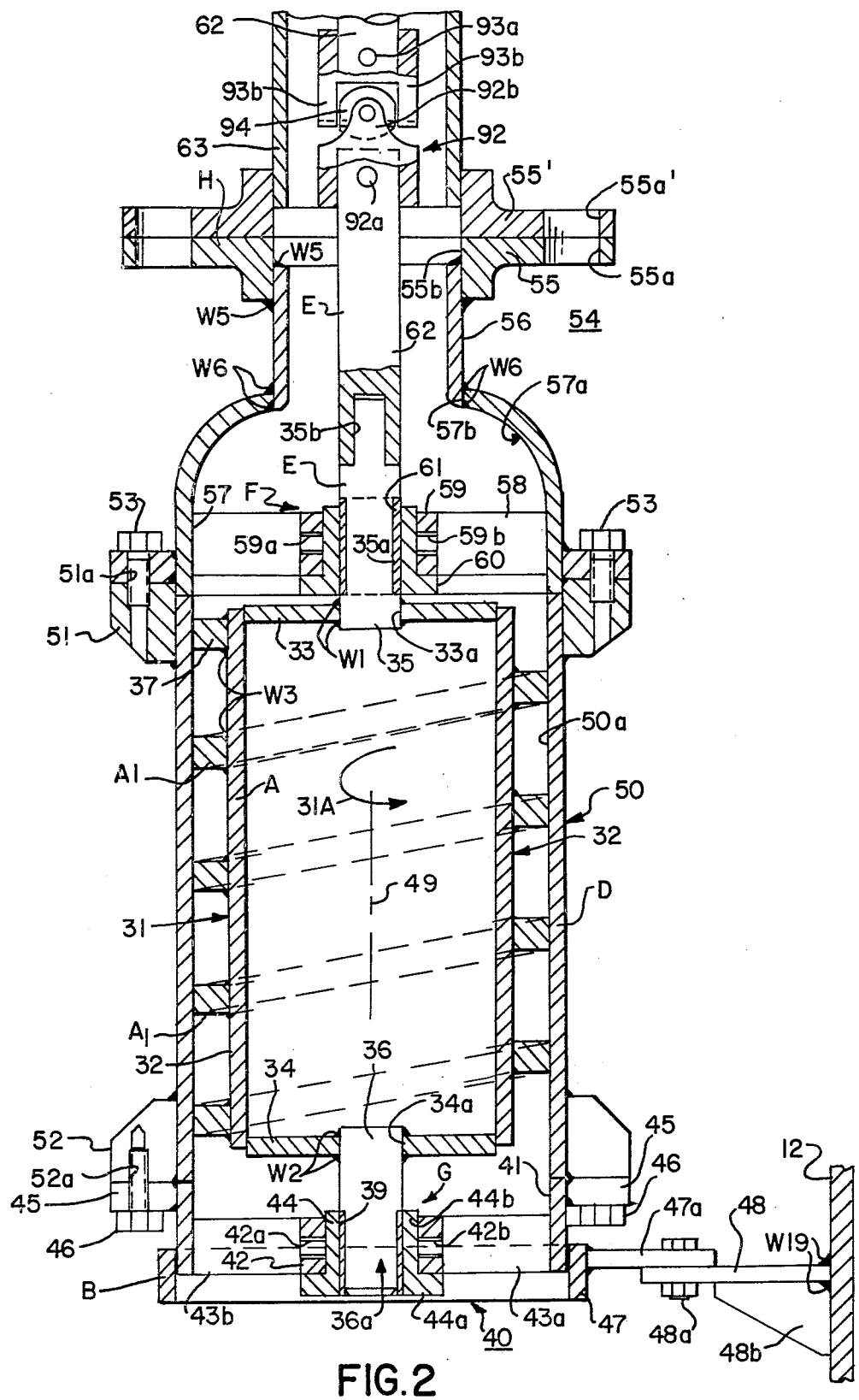
FIG. 2 shows a sectional view of the helix pump showing the pump assembly in greater detail.

The helix pump assembly 16A, as shown in detail in FIG. 2, comprises a rotor sub-assembly 31 including a hollow cylindrical shell 32 sealed at its upper and lower ends by circular discs 33 and 34, respectively. Each disc is provided with a central opening 33a, 34a for receiving and having welded thereto stub shafts 35 and 36, the weldments being shown at W1, W2, respectively.

Figure 2A:
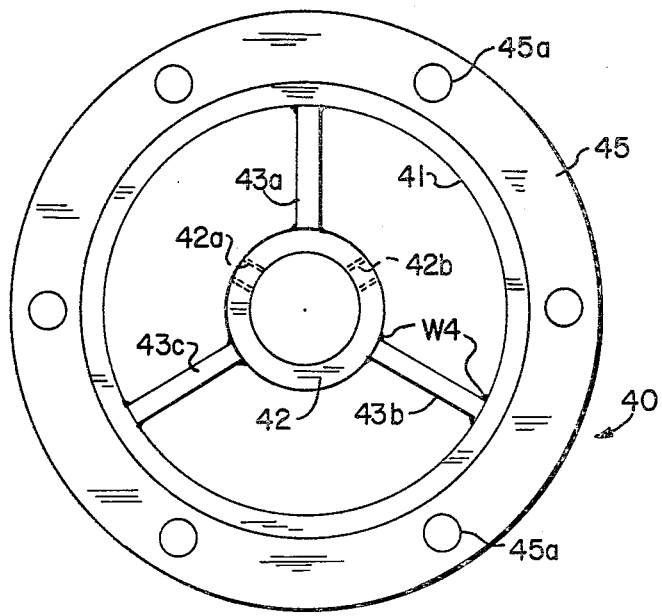
FIGS. 2a and 2b show plan views of the top and the lower guide sub-assemblies, respectively, incorporated within the helix pump assembly of FIG. 2.

The exterior surface of cylinder 32 is provided with an elongated, preferably continuous, helical coil 37 welded to cylindrical shell 32, as shown by the weldments W3. It should be noted that the direction of rotation required is shown by an arrow 31A and a right-hand helix 37 is indicated. If for some reason a left-hand helix is used, then the rotation must be reversed. The lower end of shaft 36 is provided with a portion 36a of reduced diameter. A cylindrical shaped sleeve 39 is secured to portion 36a and serves as a low friction bearing for the rotor, as will be more fully described. The shaft lower portion 36a and sleeve 39 (which may be formed of a material such a tetrafluoroethylene, for lower temperature or stellite for higher temperature) is rotatably supported by a lower shaft support assembly 40, whose bottom plan view is shown in FIG. 2a. The lower support comprises an outer cylindrical ring 41 and an inner cylindrical ring 42 joined to one another by a plurality of radially aligned equiangularly spaced ribs 43a–43c, respectively, the aforesaid elements being joined by weldments W4.

The inner ring 42 is provided with a pair of threaded openings 42a and 42b, which threadedly receive fastening members for securing a bearing sleeve 44 thereto. Bearing sleeve 44 (see FIG. 2) is provided with a flange 44a at its lower end, which is adapted to abut against the lower edge of inner ring 42.

A continuous annular flange 45 is welded to the exterior surface of outer ring 41 and is provided with a plurality of equiangular spaced openings 45a for receiving fastening means 46 which serve to join cylindrical shell 50 to the lower shaft bearing assembly.

A portion of the lower end of outer cylindrical ring 41 extends into a cylindrical shell 47 in a telescoping fashion so as to experience no "play" or wobbling when the helix pump is operating. Cylindrical ring 47 is provided with an outwardly extending supporting strut 47a for securing ring 47 to the interior wall of the tank or other support surface. Only one strut 48 need be provided, as shown in FIG. 2 to secure ring 47 against movement. The strut 48 is welded to the inner wall 12 of vessel 11 or other support surface by weldments W19. A fastening bolt or bolts 48a secures struts 47a and 48 to secure ring 47 against movement. Ring 47 prevents the helix pump assembly from experiencing movement transverse to the axis of rotation of the helix pump. The axis of the helix pump is represented by phantom line 49. A reenforcing plate 48b is provided to reenforce the mounting of strut 48 to the wall of the vessel 12.

Cylindrical shell 50 is provided with upper and lower flanges 51 and 52, respectively, each of said flanges being provided with a plurality of equi-angularly spaced tapped bores 51a, 52a for respectively receiving the fastening members 46 and 53. It should be understood that the number and spacing of openings 52a are equal to the number and spacing of the openings 45a in flange 45.

The rotor sub-assembly 31 is positioned within cylindrical shell 50 and the clearance between the helix 37 and the interior surface 50a of shell 50 is sufficient to assure free, unimpeded rotation of the rotor and yet is close enough to assure adequate lifting of the liquid contents.

Figure 2B:
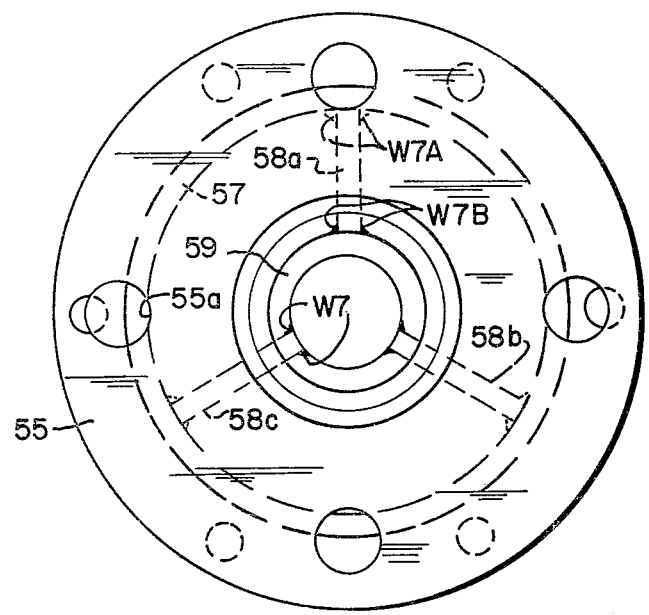

As shown in FIGS. 2, 2a and 2b the helix pump is further comprised of an upper guide assembly 54 including a circular shaped flange 55 having a plurality of equi-angularly spaced openings 55a for securement to a cooperating opening (not shown) provided at the top of the tank 11 by suitable fastening means. Flange 55 has a central opening 55b. A cylindrical shaped shell 56 telescopingly extends into the opening 55b and is secured thereto by weldment W5.

A cylindrical shell 57 has a bell-shaped upper end 57a provided with a central opening 57b for receiving the lower end of cylindrical shell 56, which is welded thereto by weldment W6. Three radially aligned equi-angularly spaced ribs 58a–58c, have their outer ends welded to the interior surface of cylindrical shell 57 by weldment W7A and have their inner ends welded to inner ring 59 by weldments W7B as shown in FIG. 2B. Inner ring 59 is provided with threaded openings 59a and 59b for receiving threaded fastening means (not shown) to secure a bearing sleeve 60 within the inner ring 59.

The upper portion 35a of shaft 35 has a reduced diameter and is adapted to receive a bearing sleeve 61 have a low coefficient of sliding friction to provide a suitable bearing assembly for rotatable upper shaft 35. A universal joint is provided to couple stub shaft 35 to drive shaft 62 to compensate for any misalignment between shafts 35 and 62. The universal joint is comprised of members 92 and 93 secured to shafts 35 and 62 by set screws 92a and 93a. An X-shaped coupling member 94 is pivotally mounted between pairs of bifurcated arms 92b and 92c. It should be understood that the bifucated arms 92b are substantially the same as arms 93b to allow tilting of shafts 35 and 62 in mutually orthogonal directions during operation of pump 16A.

The pump drive rotates shaft 62 which, through the universal joint, causes rotation of shaft 35 to rotate the rotor assembly 31 about longitudinal axis 49. The helix pump is submerged beneath the surface of the liquid batch in process. The liquid entering between the exterior surface of cylindrical shell 32 and the interior surface 50a of cylindrical shell 50 is lifted by the rotating of helix 37 along the region defined by the exterior surface of cylindrical shell 31 and the interior surface 50a of shell 50, so as to be lifted through the hollow interiors of shells 57, 57a, 56 and the hollow shaft extension housing 63 which has a diameter sufficient to enable the liquid sample being pumped vertically upward to pass between the interior surface 63a of shaft extension housing 63 and the outer periphery of shaft 62.

Figure 3:
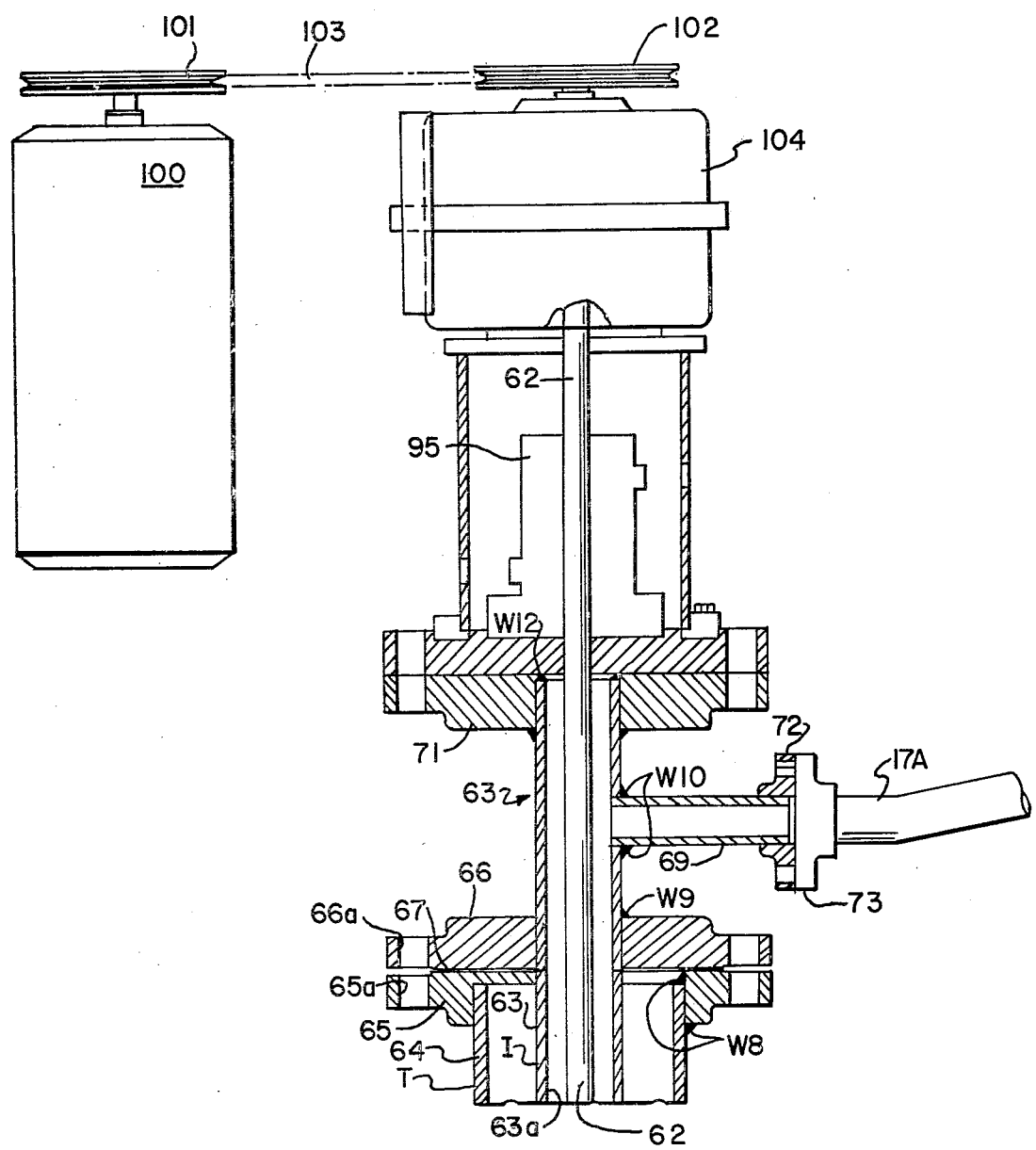
FIG. 3 shows a sectional view of the extension housing and bypass conduit of FIG. 1 in greater detail.

Turning now to a more detailed consideration of FIG. 3, the top of vessel 11 is provided with a hollow cylindrical nozzle 64 having a circular flange 65 welded thereto. Flange 65 is provided with a plurality of equiangularly spaced openings 65a and is welded to nozzle 64 as shown by weldment W8.

The extension shaft housing is fitted with a similar flange 66 welded to the housing, as shown by weldment W9, having a plurality of equi-angularly spaced openings 66a arranged to be aligned with openings 65a so as to receive suitable fastening means (not shown) for clamping the two flanges together. A suitable dis-shaped resilient sealing member 67 is sandwiched between flanges 65 and 66 to provide and air- and water-tight seal therebetween.

As was previously mentioned, it should be understood that the length of shaft extension housing 16 (although not shown for purposes of simplicity) is normally sufficient to enable the pump drive and the analytical instrumentation to be positioned at selected locations well removed from the tank 11 and wherein the instruments may even be removed from the region in which the tank 11 is situated.

Conduit 69 has one end welded to conduit 63 as shown bu weldment W10 the other end welded to flange 72, as shown by weldment W11. The upper end of the conduit 63 telescopes into and is welded to a circular flange 71, as shown by the weldments W12. The conduit 69 is coupled to conduit 17A which connection is accomplished by flanges 72 and 73, joined to one another by suitable fastening means (not shown). Conduit 17A, in turn, is coupled to a series of instruments and/or processing units such as the temperature measuring unit 18A, viscosity measuring unit 18B and other instruments 18C. Additional instrumentation may be added for measuring other characteristics. Obviously, other types of readings may be taken depending upon the type of material being processed and the characteristics desired to be monitored.

All or some of the measurements may be directly interfaced with the computer 19 which may be located on a level of the building different from that on which the batch processing is taking place. Each of the measuring units 18A–18C are connected in cascade fashion by means of intervening pipe sections. The measuring apparatus 18C is followed by a three-way valve assembly 20 having one arm 20A coupled to the outlet of unit 18C, a second arm 20C coupled to the input end of a sample extraction conduit 17C, and a final arm 20B coupled to return conduit 17B.

Three-way valve means 20 may either be operated electrically and/or mechanically to selectively extract a small sample for a type of analysis which cannot be performed in an on-line manner. The valve may, for example, have three position, namely a first position wherein the sample moves from conduit 17A to conduit 17B; a second position wherein the sample moves from conduit 17A to sample extraction pipe 17C; and a third position wherein the sample passing through conduit 17A passes to both conduits 17B and 17C. Return conduit 17C has its downstream end coupled to an opening pipe section 17D to return the majority, if not all, of the sampling fluid to the batch processing tank 11.

Since many of the materials being processed can be quite destructive, and further since the material being processed is typically quite sensitive to external influences, it is important to provide a good air- and liquid-tight seal for the tank to prevent any external influences from affecting the batch in process, and further to provide apparatus which will not in any way affect the quality and consistency of the batch in process. For example, the drive is preferably of the self-lubricating type to prevent any lubricant from entering into, and possibly deleteriously affecting the batch in process. In the arrangement shown, the drive for extracting a liquid stream from the vessel is comprised of motor 100 having an output pulley 91 coupling rotation to pulley 92 by belt 93. Pulley 102 drives shaft rotation reducing means 104 which drives the pump extension shaft 62. A stuffing box assembly 105 prevents the batch being processed, which may be highly viscous and highly adherent, from contacting the shaft rotation reducing means 104. If desired, the stuffing box assembly may be replaced by a mechanical seal.

In operation, the pump drive 104 is designed to rotate at relatively low output speeds, typically of the order of 300 to 1800 rpm, to continuously lift liquid from the batch being processed upwardly from the region between rotor sub-assembly 31 and cylindrical shell 50, and through extension housing 63 whereupon the liquid is caused to pass through the bypass conduit 69 and through the conduits 69 and 17A coupling each of the analytical instruments. The valve 20 is provided to terminate flow in cases where repairs or maintenance are required to the instruments or to the conduit feeding the sample to the instrumentation. The flow continues through each of the instruments by way of conduit 17A and normally all of the sample is returned to the batch processing tank. A typical flow rate through the external branch is in the range from 0.25 gallons per minute to 2.5 gallons per minute although other ranges may be provided depending upon the particular application. The typical amount needed for extraction of a sample is of the order of one pint of liquid. By operating continuously, the external branch is assured of being cleared of any old solution as well as providing a generally self-cleansing effect, thus assuring the up-to-date samples are provided during the testing intervals. Also, continuous operation permits continuous instantaneous monitoring by the instrumentation.

The helix pump is self-draining as are the conduits 17A and 17B. Substantially all of the liquid will drain from the pump assembly 16A when the liquid is removed from the tank. The outside diameter of upper and lower flanges 51, 52 of the sample pump shell are smaller than the inside diameter of vessel nozzle neck 64 and by disconnecting flanges 72, 73 and 65, 66 the entire sample pump 16A may be lifted out of the vessel 11. Then by removing the fastening members 46 and 53, the rotor assembly 51 may be made accessible and cleaned when desired, as well as the upper and lower bearing assemblies 49 and 54 and the cylindrical shell 50.

The design of the helix pump enables its use within pressurized tanks so as to eliminate the introduction of any air or external contaminants. A good flow rate is obtained through a motor having a low running speed due to the fact that the helix pump provides excellent "lifting" capabilities.

While the invention has been described with a certain degree of particularly, it will be understood that the description was by way of example only and that numerous variations and modifications, as may become apparent to those of ordinary skill in the art, can be made without departing from the spirit and the scope of the invention as hereinafter claimed. For example, the helix pump may be replaced by a positive displacement, progressive type cavity pump.

What is claimed is:

1. A system for monitoring a chemical composition being processed in a vessel, comprising:

pump means positioned in the vessel and being submerged below the surface of the chemical composition being processed;

pump drive means being positioned above and external to said vessel;

an elongated shaft extending downwardly from said drive means to said pump means and coupling the output of said drive means to said pump means;

an elongated housing connected to said pump means to permit the upward flow of a sample therethrough;

said elongated housing having a branching conduit for receiving said sample, said branching conduit further including a return conduit portion for returning the liquid sample introduced into said return conduit by said branching conduit to said vessel, whereby said pump means provides a continuous flow through said branching and return conduits; and means communicating with the fluid sample passing through said branching conduit for monitoring at least one predetermined characteristic of said sample.

2. The system of claim 1, wherein said pump means is a positive displacement cavity-type pump.

3. The system of claim 1, wherein said pump means is a helix pump.

4. The system of claim 1, wherein means are provided between the output end of said drive means and the upper end of said shaft and said elongated shaft housing for coupling rotational drive from said drive means to said elongated coupling shaft and for sealing said drive means from the contents of said tank, and to further maintain the integrity of the pressure condition of said vessel in the region of the rotating seal.

5. The system of claim 4, wherein said sealing means comprises a stuffing box assembly.

6. The system of claim 4, wherein said stuffing box is a mechanical seal.

7. The system of claim 3, wherein said helix pump comprises:

a cylindrical shaped rotor;

a continuous projection extending outwardly from the surface of said cylindrical rotor and defining a helix whose longitudinal axis is co-linear with the axis of rotation with said rotor;

a hollow cylindrical shell having an inner diameter slightly greater than the outer diameter of said helix, said rotor being positioned within said shell whereby the aforementioned clearance allows free, unimpeded rotation of said rotor within said shell; and coupling means extending between the upper end of said shell and the lower end of said extension housing whereby liquid lifted upwardly by said helix pump, and in the region between the exterior of the cylindrical rotor and the interior surface of said cylindrical shell, is conveyed upwardly through said extension housing.

8. The system of claim 7, wherein said helix pump further comprises:

upper and lower bearing assemblies for rotatably mounting said rotor in a free-wheeling manner;

means for securing the upper bearing assembly to said tank; and collar means secured to said tank and positioned a spaced distance below said upper bearing securing means telescopingly receiving said lower bearing assembly when the helix pump is in its operative position within the tank to prevent the lower bearing assembly and hence the drive motor from experiencing any wobbling.

9. The system of claim 1, further comprising valve means positioned along said branching conduit for controlling flow and rate of flow of the liquid sample from said extension housing into said branching conduit means.

10. The system of claim 1, further comprising three-way valve means in said branching conduit for enabling extraction of a portion of the fluid sample passing through said branching conduit for purposes of "off-line" analysis.

11. The system of claim 1, wherein additional analysis means are provided and sectional conduit means are provided for coupling said additional analysis means in sequential fashion along said branching conduit enabling each of said analysis means to directly communicate with the liquid sample for analytical and monitoring purposes.

12. The system of claim 11, further comprising computer means for analyzing data collected by all of said monitoring means.

13. The system of claim 12, further comprising heating means, agitation means, and means responsive to said computer for controlling said heating and agitation means at predetermined intervals in said batching process.

14. The system of claim 1, wherein said branching and return conduits are arranged to slope upwardly and away from the vessel to provide a self-draining feature when the vessel is being emptied.

15. The system of claim 1, further including a conduit for extracting a sample for off-line analysis;

three-way valve means and having three positions, wherein said branching and return conduits are in communication when the valve means is operated to its first position and said branching conduit and one end of said sample extracting conduit are in communication when said valve means is in a second position.

16. The system of claim 15, wherein said three-way valve means further comprises a third position wherein said branching conduit is simultaneously in communication with both said return conduit and said sample extraction conduit.

* * * * *